United States Patent [19]
Blair

[11] Patent Number: 4,757,554
[45] Date of Patent: Jul. 19, 1988

[54] SKIERS SAFETY HARNESS

[76] Inventor: George A. Blair, 135 N. Lake Florence Dr., Winter Haven, Fla. 33884

[21] Appl. No.: 882,481

[22] Filed: Jul. 7, 1986

[51] Int. Cl.⁴ ............................................. A61F 5/00
[52] U.S. Cl. ................................................. 2/2; 2/44; 128/68.1
[58] Field of Search ........ 128/380, 78, 68.1, DIG. 23; 2/44, 45, 422, 425; 297/393

[56] References Cited

U.S. PATENT DOCUMENTS

| 382,949 | 5/1888 | Campbell | 297/393 |
| 1,510,187 | 9/1924 | Martin | 128/DIG. 23 |
| 2,735,424 | 2/1956 | Benjamin | 128/DIG. 23 |
| 2,973,030 | 2/1961 | Matthewson | 297/393 |
| 3,189,917 | 6/1965 | Sims | 128/DIG. 23 |
| 3,889,668 | 6/1975 | Ochs et al. | 2/44 |
| 4,034,747 | 7/1977 | Leroy | 128/DIG. 23 |

Primary Examiner—Louis K. Rimrodt
Attorney, Agent, or Firm—Roger A. Clapp

[57] ABSTRACT

Apparatus is disclosed in which a pair of back straps, a pair of neck straps and a linking web combine to hold a neck cushion in place for protecting the neck of an athlete such as a water skier or the like.

2 Claims, 2 Drawing Sheets

SKIERS SAFETY HARNESS

BACKGROUND OF THE INVENTION

1. FIELD OF THE INVENTIONS

The invention relates to harness devices and pertains to those in which a neck brace is strapped to the body to protect the wearer against injury such as whip lash.

2. DESCRIPTION OF THE PRIOR ART

Atheletes in strenuous sports are continuously risking serious bodily injury. In water skiing, however, one aspect of the risk has received no attention. Specifically, when a skier performs or falls, he or she is subject to dangerous cervical injury because of the sharply opposing forces which are often generated.

Accordingly, an object of this invention is to improve the protection of athletes from cervical and other spinal injuries as they perform.

The means of protection, however, must be convenient to use or it will be ignored. Moreover, it must be simple in construction and inexpensive to fabricate.

Accordingly, another object of this inventioan is to achieve injury protection in a convenient, simple and inexpensive way.

SUMMARY OF THE INVENTION

In accordance with the preferred embodiment of the invention, a neck strap assembly supports a cervical pad and a central web links the shoulder strap assembly with a back strap assembly to form a protective harness.

In accordance with one feature of the invention, the neck strap assembly has two ends designed to overlap across the chest of a user, each end thereof includes part of a locking mechanism, the back strap assembly has two ends designed to overlap across the chest of a user, and each end includes the mating part of each part of the locking device located on the neck strap ends whereby connection between the two assemblies can be made quickly and easily.

In accordance with another feature of the invention, the back and neck strap assemblies wrap tightly under the armpits of the user so as to form a tight and firm fit between the neck of the user and the cervical pad.

A better understanding of these and other objects and features will be facilitated by reference to the following description of the drawing and detailed description of the invention.

BRIEF DESCRIPTION OF THE INVENTION

DETAILED DESCRIPTION OF THE INVENTION

Figure 1:
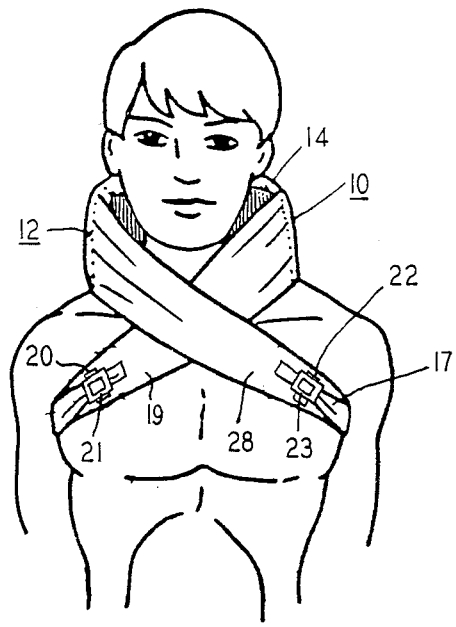
FIG. 1 is a front elevation view of an athlete shown wearing a harness made in accordance with the invention.
Figure 3:
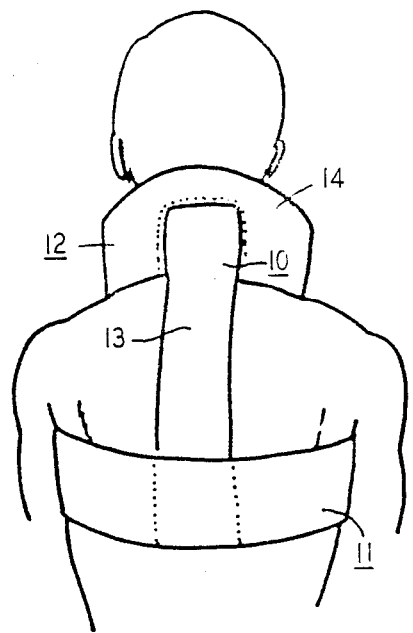
FIG. 3 is a real elevation of the athlete depicted in FIGS. 1 and 2 and is shown wearing a harness in accordance with the invention.
Figure 4:
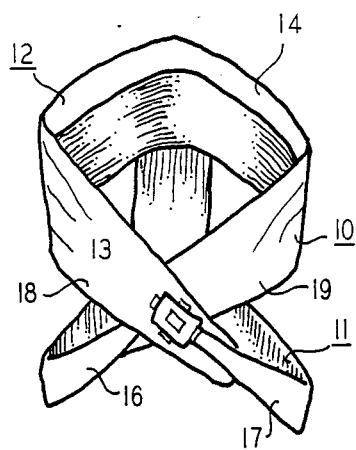
FIG. 4 is a front elevation view taken in perspective of an alternate form of the harness shown in FIGS. 1, 2 and 3 wherein the straps have been overlapped as they would be on a typical user.
Figure 5:
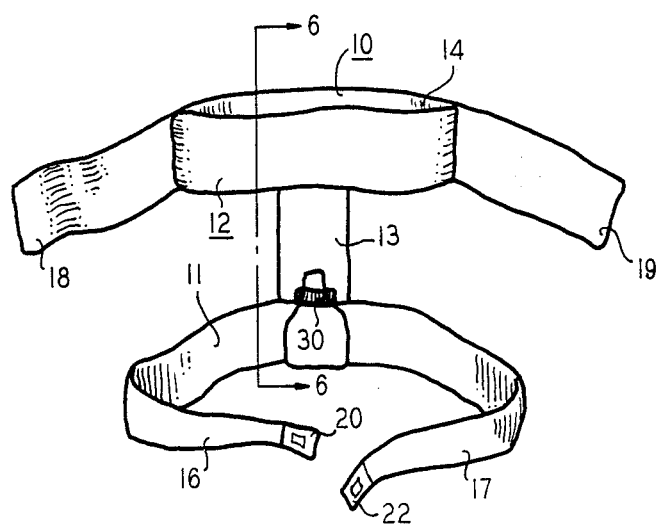
FIG. 5 is a front elevation view of the harness illustrated in FIGS. 1, 2 and 3 wherein the harness has been spread out to show its components.

Referring to FIG. 1, an athlete is depicted wearing a harness assembly 10 made in accordance with this invention. As best seen in FIGS. 3, 4 and 5, the harness assembly 10 comprises a back strap assembly 11, a neck strap assembly 12 and a linking web 13. All of the components are designed to be worn against the body and may conveniently be made of a strong, durable material such as nylon or the like.

Figure 2:
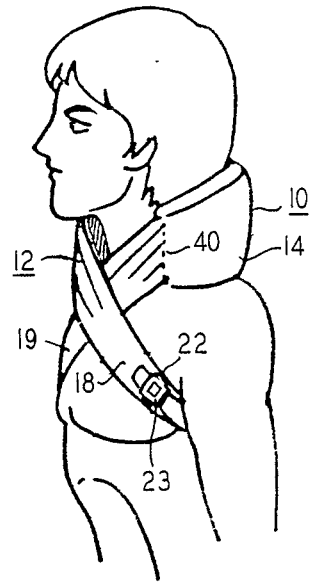
FIG. 2 is a side elevation view of the athlete depicted in FIG. 1 and is shown wearing a harness in accordance with the invention.
Figure 6:
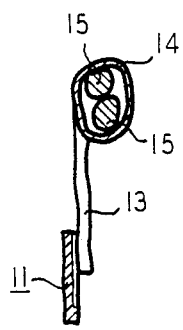
FIG. 6 is a side elevation view of the harness shown in FIG. 5 taken in section along the line 6—6.

Again, as best seen in FIGS. 3, 4 and 5, the back strap assembly 11 includes a neck pad 14. As illustrated in FIGS. 2 and 4, the neck pad 14 may be a solid unitary structure or, as as shown in FIG. 6, it may comprise a composite structure formed by a roll of material such as nylon or the like encircling one or more padded members or cylinders 15. Advantageously, the material of the solid neck pad 14 or cylinders 15 is a soft, energy absorbent material such as foam polyester or the like.

Where one or more padded cylinders 15 are used, the linking web 13 can directly encircle the cylinders 15. In the alternative, the cylinders 15 can be separately encapsulated and then the resulting package encircled by or joined to the web 13.

The back strap assembly 11 and the neck strap assembly 12 are elongated and terminate in the ends 16, 17, 18 and 19, respectively. Moreover, as shown in FIGS. 1 and 2, the ends all including portions of a harness locking system. Specifically, the ends 16 and 17 each include portions 20 and 21 of a lock and the ends 18 and 19 include portions 22 and 23 which complete the lock when engaged with the portions 20 and 21, respectively.

The portions 22 and 23 may, for example, be the female parts of a standard lock of the type commonly used to fasten seat belts. In that case, the portions 20 and 21 may advantageously be the male parts. In any event, the portions 22 and 23 are attached to the back strap assembly at an intermediate position on the ends 18 and 19 so that the ends 18 and 19 will overlap the ends 16 and 17 when they are engaged as shown in FIG. 3. Alternatively, as shown in FIG. 4, the locking mechanism can be fabricated from mating pairs of "Velcro" or similar connecting materials.

In the embodiment disclosed, the linking web 13 is sewn to the back strap assembly 11 and the neck strap assembly 12 to form a unitary harness. As illustrated in FIGS. 1, 2 and 3, the web 13 is short enough so as to cause the ends of the back and neck strap assemblies to form a tight fit under the armpits of the user. As further illustrated in FIGS. 3, 5 and 6, the web 13 may advantageously be looped around either the neck strap assembly or the back strap assembly 11 and be adjustably attached by means of an appropriate locking assembly 30.

In use, an athlete such as a water skier places the harness assembly 10 on his back and positions the neck pad 14 behind his or her neck. Thereafter, the web 13 is adjusted if so fabricated, and the ends 16 and 17 are joined to the ends 18 and 19 so as to form a snug fit under the armpits of the athlete and he or she is ready to engage in the desired activity.

The harness is advantageously used to protect against all kinds of whip lash type injuries; i.e., race car driving, boat racing and similar sports where the athlete's body can be unexpectedly subjected to severe and opposing forces. It is especially useful by water skiers who are skiing barefoot particularly where the skier is skiing on one foot and the other is joined to the tow rope. When skiiing that way, if the skier's supporting leg penetrates the water, his or her body will pivot and cause a fall in the direction of travel. When that happens, the skier's body hits the water, suddenly stops, and his or her head continues in the direction of the fall. As a result, the skier will be subjected to whip lash. If the skier is wearing the harness, however, his or her head will be cushioned by the neck pad 14 so as to avoid or minimize injury.

In another embodiment, the neck pad 14 is somewhat elongated so that it will be drawn up under or near the jaw line of the wearer when strapped in place; i.e., so that the junction 40, as shown in FIG. 2, is moved forward with respect to the wearers chin to bring the padded portion under the wearer's jaw line and thereby oppose both both forward and sideward, as well as rearward, rotation or movement of the wearers head. In that embodiment, forward, sideward, rearward and various combinations of whip lash in all directions will be cushioned, retarded or eliminated. In addition, the upper ridge of the pad 14 can be alinged under head gear worn by the athlete; i.e., under a helmet worn by a football player or the like to further retard or prevent whiplash movement.

In summary, a protective harness has been disclosed which readily protects the wearer from cervical injury in a simple and convenient fashion. While only one embodiment of the invention has been disclosed, it will be recognized that the embodiment is merely exemplary of the principals of the invention and may other embodiments falling within the ambit of the invention will readily occur to those skilled in the art.

What I claim is:

1. In harness apparatus for protecting an athlete from cervical injury, the combination comprising:
    pad means for preventing an athlete's head and neck from moving freely in a back and forth plane,
    neck strap means for holding said pad means against the athlete's neck, said neck strap means being adapted to diagonally criss-cross over a portion of the athlete's upper chest and comprising two elongated neck straps each having first and second ends, said first ends being afixed to said pad means and said second ends including first attaching means,
    back strap means for holding said harness apparatus on the athlete's body and tightly under his or her armpits in cooperation with said neck strap means, said back strap means comprising two elongated back straps each having first and second ends, said second ends adapted to extend under the arm pits and diagonally across said upper portion of the athlete's chest and including second attaching means adapted to attach to said first attaching means on said neck straps over the athlete's chest so that said back straps and neck straps diagonally criss-cross in coextensive relationship over the athlete's upper chest when joined, and
    web means for linking said pad means, said neck strap means and said back strap means into a unitary harness assembly, said web means being made of a flexible cloth-like material and said pad means and said first back strap ends being connected to said web means.

2. The combination in accordance with claim 1 wherein said pad means comprises a cloth roll encapsulating one or more cylinders of soft material suitable for cushioning the cervical area or a user from injury.

* * * * *